(12) United States Patent
Miura et al.

(10) Patent No.: US 12,329,554 B2
(45) Date of Patent: Jun. 17, 2025

(54) RADIATION IMAGING APPARATUS

(71) Applicant: CANON KABUSHIKI KAISHA, Tokyo (JP)

(72) Inventors: Ryosuke Miura, Chiba (JP); Naoto Takahashi, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 249 days.

(21) Appl. No.: 18/054,836

(22) Filed: Nov. 11, 2022

(65) Prior Publication Data

US 2023/0168394 A1   Jun. 1, 2023

(30) Foreign Application Priority Data

Nov. 26, 2021   (JP) .................................. 2021-192186

(51) Int. Cl.
 *A61B 6/42*   (2024.01)
 *A61B 6/00*   (2024.01)

(52) U.S. Cl.
 CPC ............ *A61B 6/4291* (2013.01); *A61B 6/542* (2013.01)

(58) Field of Classification Search
 CPC .............................. A61B 6/4291; A61B 6/542
 See application file for complete search history.

(56) References Cited

U.S. PATENT DOCUMENTS

2013/0140465 A1*   6/2013  Nishinou ............... G03B 42/02
                                                          250/366
2015/0030129 A1*   1/2015  Tajima .................. A61B 6/4291
                                                          378/62

FOREIGN PATENT DOCUMENTS

JP               5969950 B2      8/2016

* cited by examiner

*Primary Examiner* — Chih-Cheng Kao
(74) *Attorney, Agent, or Firm* — Canon U.S.A., Inc., IP Division

(57) ABSTRACT

A radiation imaging apparatus that is able to perform radiography using a grid in which a radiation transmissive layer and a radiation absorption layer each having a strip shape and extending in a first direction are alternately arranged in a second direction, the radiation imaging apparatus includes a pixel unit including a plurality of imaging pixels and a plurality of detection pixels, wherein the plurality of detection pixels includes a first detection pixel and a second detection pixel that are in a pair in the second direction, an output signal value of the first detection pixel is larger than an average value of output signal values of the plurality of imaging pixels and the plurality of detection pixels, and an output signal value of the second detection pixel is smaller than the average value.

5 Claims, 12 Drawing Sheets

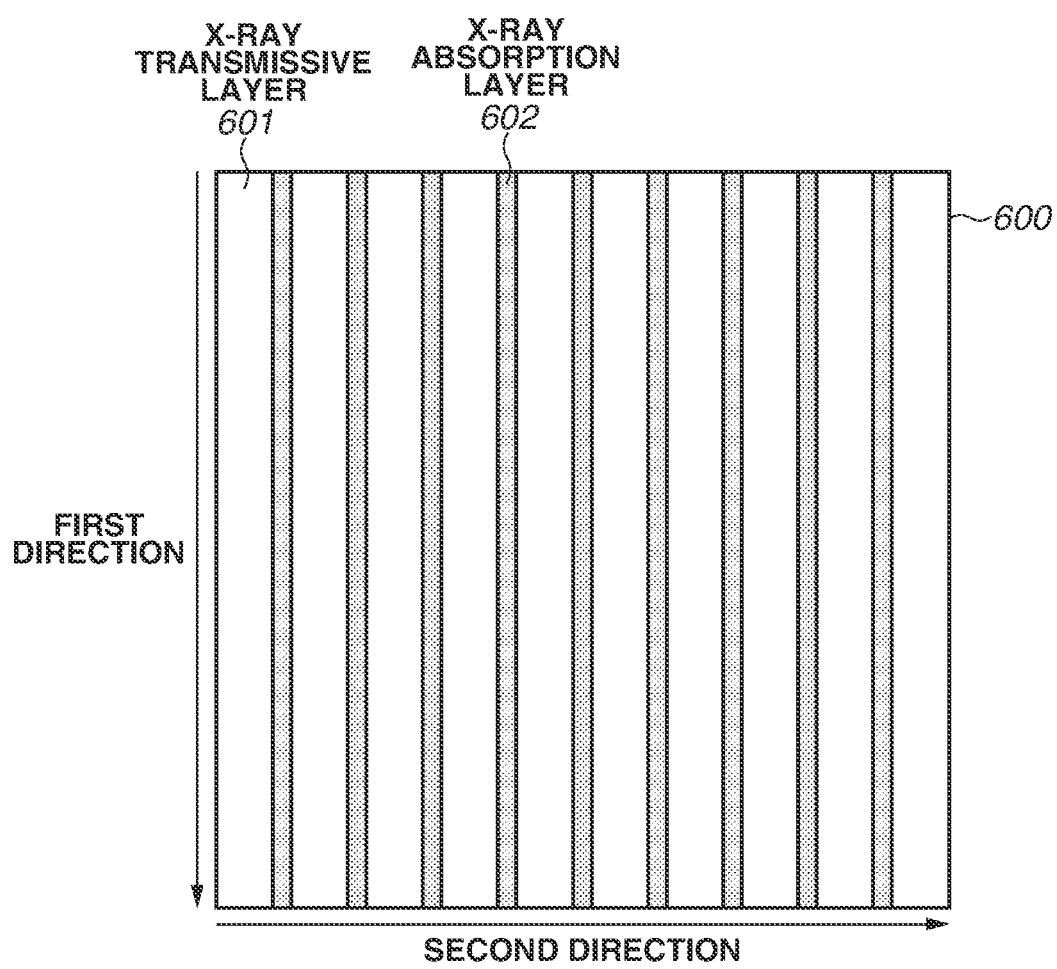

RADIATION IMAGING APPARATUS

BACKGROUND OF THE INVENTION

Field of the Invention

The present invention relates to a radiation imaging apparatus.

Description of the Related Art

Radiation imaging apparatuses having an automatic exposure control (AEC) function are known. Such a radiation imaging apparatus can measure a dose of radiation during emission, and based on a result of the measurement, the emission of radiation is terminated. For example, the radiation imaging apparatus monitors a dose of radiation by operating only pixels set for radiation detection at high speed during the emission of radiation.

Meanwhile, in X-ray imaging, scattered rays are generated when X-rays pass through an object. To remove the scattered rays, a grid is generally used. The grid has a structure in which an X-ray transmissive layer and an X-ray absorption layer each having a strip shape are alternately arranged, and the grid is disposed between the object and the imaging apparatus during image capturing.

Because of an overlap between the X-ray absorption layer of the grid and radiation detection pixels, some radiation detection pixels may detect a signal corresponding to an X-ray attenuated by the X-ray absorption layer. Depending on a pixel size, an arrangement of radiation detection pixels, and an array pitch of X-ray absorption layers of the grid, there may be a disproportionate influence on signals of the plurality of radiation detection pixels in a region of interest due to attenuation by the X-ray absorption layers of the grid. In this case, a discrepancy arises between an average dose of radiation in the region of interest and signals corresponding to a dose of radiation detected by the radiation detection pixels, which leads to deterioration of the accuracy of the automatic exposure control.

Japanese Patent No. 5969950 discusses a radiation imaging apparatus in which periodicity in the arrangement of dose detection sensors and periodicity in the arrangement of radiation absorption portions of a grid are different from each other. This configuration is to suppress a disproportionate influence on the dose detection sensors due to dose attenuation by the grid even in a case where the positional relationship between the dose detection sensors and the grid changes. In the technique of Japanese Patent No. 5969950, however, there may be room for an improvement in the configuration to further decrease the disproportionate influence on the dose detection sensors due to the dose attenuation by the grid.

SUMMARY OF THE INVENTION

The present invention is directed to providing a technology for improving the accuracy of automatic exposure control, by reducing or suppressing a disproportionate influence on signals of a plurality of radiation detection pixels in a region of interest due to attenuation by an X-ray absorption layer of a grid.

According to an aspect of the present invention, a radiation imaging apparatus that is able to perform radiography using a grid in which a radiation transmissive layer and a radiation absorption layer each having a strip shape and extending in a first direction are alternately arranged in a second direction, the radiation imaging apparatus includes a pixel unit including a plurality of imaging pixels for acquiring a radiation image and a plurality of detection pixels for detecting a dose of radiation that are disposed in an imaging region, a driving unit configured to drive the plurality of imaging pixels and the plurality of detection pixels, a reading unit configured to read out a signal from each of the plurality of imaging pixels and the plurality of detection pixels, and a control unit configured to determine an amount of radiation being emitted to the radiation imaging apparatus, wherein the plurality of detection pixels includes a first detection pixel and a second detection pixel that are in a pair in the second direction, an output signal value of the first detection pixel is larger than an average value of output signal values of the plurality of imaging pixels and the plurality of detection pixels, and an output signal value of the second detection pixel is smaller than the average value.

According to another aspect of the present invention, a radiation imaging apparatus includes a pixel unit including a plurality of imaging pixels for acquiring a radiation image and a plurality of detection pixels for detecting a dose of radiation that are disposed in an imaging region, a driving unit configured to drive the plurality of imaging pixels and the plurality of detection pixels, a reading unit configured to read out a signal from each of the plurality of imaging pixels and the plurality of detection pixels, and a control unit configured to determine an amount of radiation being emitted to the radiation imaging apparatus, wherein the plurality of detection pixels includes a first detection pixel and a second detection pixel, and in a case where radiography is performed using a grid in which a radiation transmissive layer and a radiation absorption layer each having a strip shape and extending in a first direction are alternately arranged in a second direction, the first detection pixel and the second detection pixel are disposed in a pair in the second direction in such a manner that an output signal value of the first detection pixel is larger than an average value of output signal values of the plurality of imaging pixels and the plurality of detection pixels and an output signal value of the second detection pixel is smaller than the average value.

According to yet another aspect of the present invention, the average value of the output signal values of the plurality of imaging pixels and the plurality of detection pixels is an average value of output signal values of an imaging pixels and a detection pixels located disposed in a detection area that is an area where radiation is to be detected.

According to yet another aspect of the present invention, an average value of the output signal values of the first detection pixel and the second detection pixel is equal to the average value of the output signal values of the plurality of imaging pixels and the plurality of detection pixels.

According to yet another aspect of the present invention, the first detection pixel and the second detection pixel are disposed, in the second direction, at respective positions satisfying the following equation:

$$C = (1+2n)/fg,$$

where $$fg = 2|D \times P/10 - k|,$$

where C represents a position of the second detection pixel with respect to the first detection pixel, D represents a grid density (number/centimeter), P represents a pixel pitch (millimeter), k represents an integer satisfying $0 \leq fg \leq 1$, and n represents an integer of 0 or more.

According to yet another aspect of the present invention, a plurality of pairs of the first detection pixel and the second detection pixel are disposed.

According to yet another aspect of the present invention, the plurality of pairs of the first detection pixel and the second detection pixel is disposed in an aperiodic arrangement.

Further features of the present invention will become apparent from the following description of exemplary embodiments with reference to the attached drawings.

BRIEF DESCRIPTION OF THE DRAWINGS

FIG. 7 is a diagram illustrating a grid according to the first exemplary embodiment of the present invention.

DESCRIPTION OF THE EMBODIMENTS

Figure 1:
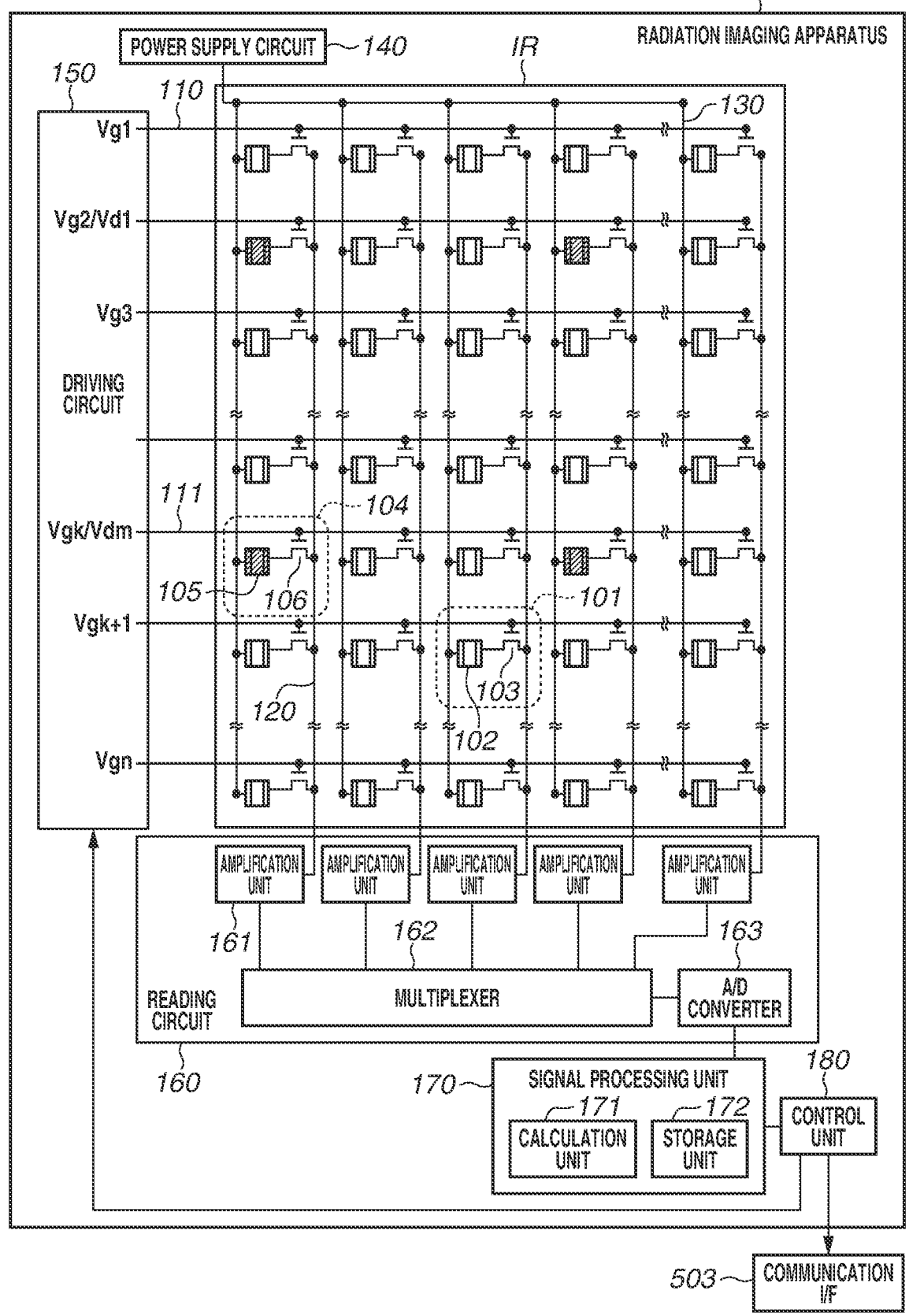
FIG. 1 is a diagram illustrating a configuration of a radiation imaging apparatus according to a first exemplary embodiment of the present invention.

Exemplary embodiments of the present invention will be described below with reference to the attached drawings. Similar components are denoted by the same reference numerals through various exemplary embodiments, and the redundant descriptions will not be repeated. The exemplary embodiments can be modified and combined as appropriate.

FIG. 1 illustrates an example of a configuration of a radiation imaging apparatus 100 capable of performing radiography using a grid, according to a first exemplary embodiment of the present invention. The radiation imaging apparatus 100 has a plurality of pixels, which is arranged in an imaging region IR in a form of a plurality of rows and a plurality of columns, a plurality of driving lines 110, and a plurality of signal lines 120. The plurality of driving lines 110 is disposed to correspond to the plurality of rows of pixels, and each of the driving lines 110 corresponds to a different one of the pixel rows. The plurality of signal lines 120 is disposed to correspond to a plurality of columns of pixels, and each of the signal lines 120 corresponds to a different one of the pixel columns.

The plurality of pixels includes a plurality of imaging pixels 101, which is used to acquire a radiation image, and one or more detection pixels 104 (hereinafter may also be referred to as the radiation detection pixels 104), which is used to monitor a dose of radiation, and a pixel unit is formed of the imaging pixels 101 and the detection pixels 104.

The imaging pixel 101 includes a conversion element 102 for converting radiation into an electrical signal and a switch element 103 for connecting the corresponding signal line 120 and the conversion element 102. The detection pixel 104 includes a conversion element 105 for converting radiation into an electrical signal and a switch element 106 for connecting the corresponding signal line 120 and the conversion element 105. The detection pixel 104 is disposed in a row and a column formed of the plurality of imaging pixels 101. In FIG. 1 and subsequent figures, the conversion element 102 is not hatched and the conversion element 105 is hatched so as to be distinguishable between the imaging pixel 101 and the detection pixel 104.

The conversion element 102 and the conversion element 105 can each be composed of a scintillator for converting radiation into light and a photoelectric conversion element for converting the light into an electrical signal. In general, the scintillator is formed in a sheet form covering the imaging region IR and shared by a plurality of pixels. Alternatively, the conversion element 102 and the conversion element 105 can each be configured of a conversion element that directly converts radiation into an electrical signal.

The switch element 103 and the switch element 106 can each include a thin-film transistor (TFT) in which an active region is formed of a semiconductor, such as an amorphous silicon or a polycrystalline silicon.

A first electrode of the conversion element 102 is connected to a first main electrode of the switch element 103, and a second electrode of the conversion element 102 is connected to a bias line 130. The bias line 130 extends in a column direction and is commonly connected to the second electrodes of the plurality of conversion elements 102 arranged in the column direction. The bias line 130 receives a bias voltage Vs from a power supply circuit 140. Second main electrodes of the switch elements 103 of the one or more imaging pixels 101 included in one column are connected to the signal line 120. Control electrodes of the switch elements 103 of the one or more imaging pixels 101 included in one row are connected to the driving line 110.

The detection pixel 104 also has a pixel configuration similar to the configuration of the imaging pixel 101 and is connected to the corresponding driving line 110 and the corresponding signal line 120. The imaging pixel 101 can be connected to the same signal line 120 as that of the detection pixel 104.

A driving circuit 150 constituting a driving unit is configured to supply a driving signal to a driving target pixel, through each of the plurality of driving lines 110, based on a control signal from a control unit 180. In the present exemplary embodiment, the driving signal is a signal that turns on the switch element included in the driving target pixel. The switch element of each of the pixels is turned on by a signal at high level and turned off by a signal at low level. Thus, the signal at high level will be referred to as the driving signal. Supplying the driving signal to the pixel results in a state where signals accumulated in the conversion element of the pixel can be read out by a reading circuit 160. Among the driving lines 110, the driving line 110 connected to the detection pixel 104 will be referred to as a detection driving line 111.

The reading circuit 160 is configured to read out signals from the plurality of pixels through the plurality of signal lines 120. The reading circuit 160 includes a plurality of amplification units 161, a multiplexer 162, an analog-to-digital converter (hereinafter referred to as the A/D converter) 163. Each of the plurality of signal lines 120 is connected to the corresponding amplification unit 161 among the plurality of amplification units 161 of the reading circuit 160. The signal line 120 corresponds to the amplification unit 161 on a one-on-one basis. The multiplexer 162 selects the plurality of amplification units 161 in a predetermined order and supplies a signal from the selected amplification unit 161 to the A/D converter 163. The A/D converter 163 converts the supplied signal into a digital signal and outputs the digital signal.

The signals read out from the imaging pixels 101 are supplied to a signal processing unit 170 and subjected to processing, such as calculation and storage, by the signal processing unit 170. Specifically, the signal processing unit 170 includes a calculation unit 171 and a storage unit 172, and the calculation unit 171 generates a radiation image based on the signals read out from the imaging pixels 101 and supplies the generated radiation image to the control unit 180. The signals read out from the detection pixels 104 are supplied to the signal processing unit 170 and subjected to processing, such as calculation and storage, by the calculation unit 171. Specifically, the signal processing unit 170 outputs information indicating emission of radiation to the radiation imaging apparatus 100, based on the signals read out from the detection pixels 104. For example, the signal processing unit 170 detects emission of radiation to the radiation imaging apparatus 100 and determines a dose and/or an integrated dose of radiation.

The control unit 180 controls the driving circuit 150 and the reading circuit 160, based on information from the signal processing unit 170. The control unit 180 controls, for example, a start and an end of exposure (accumulation of electric charges corresponding to emitted radiation in the imaging pixels 101), based on the information from the signal processing unit 170.

To determine a dose of radiation, the control unit 180 scans the detection driving line 111 by controlling the driving circuit 150, so that only the signal of the detection pixel 104 can be read out. Next, the control unit 180 reads out signals of a column corresponding to the detection pixel 104 by controlling the reading circuit 160 and outputs the signals as information indicating the dose of radiation. Such operation makes it possible for the radiation imaging apparatus 100 to obtain emission information in the detection pixel 104 during emission of radiation.

Figure 2:
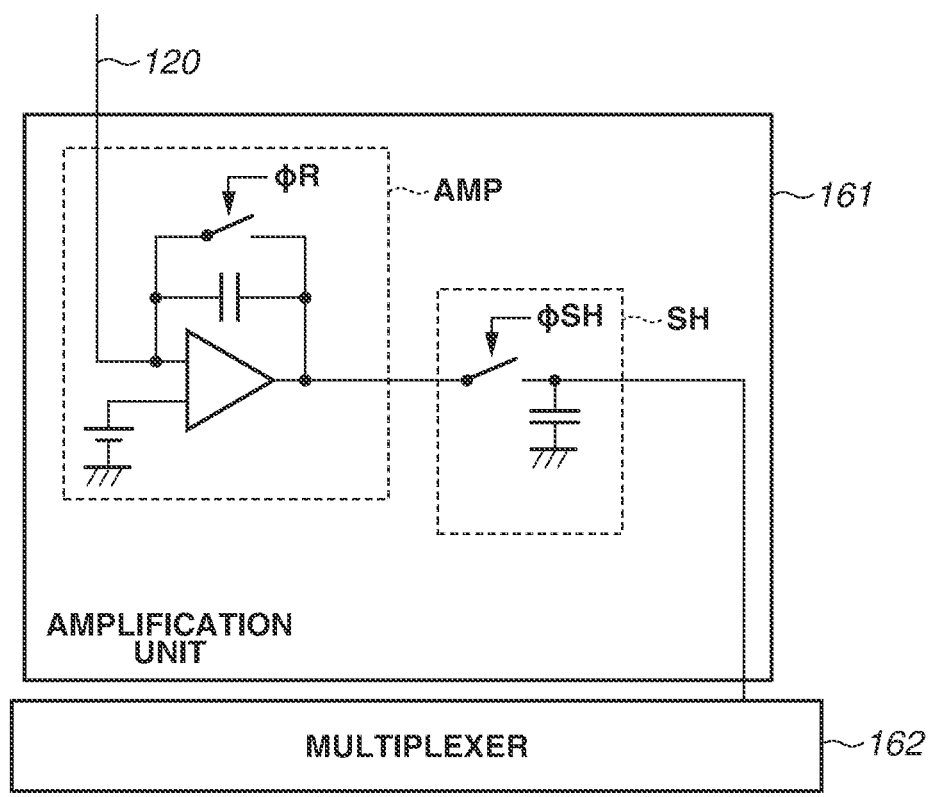
FIG. 2 is a diagram illustrating a configuration of an amplification unit according to the first exemplary embodiment of the present invention.

FIG. 2 illustrates an example of a detailed circuit configuration of the amplification unit 161. The amplification unit 161 includes a differential amplification circuit AMP and a sample hold circuit SH. The differential amplification circuit AMP amplifies a signal appearing on the signal line 120 and outputs the amplified signal. The control unit 180 can reset the potential of the signal line 120 by supplying a control signal φR to a switch element of the differential amplification circuit AMP. The output from the differential amplification circuit AMP can be held by the sample hold circuit SH. The control unit 180 causes the sample hold circuit SH to hold the signal by supplying a control signal φSH to a switch element of the sample hold circuit SH. The signal held by the sample hold circuit SH is read out by the multiplexer 162.

Figure 3:
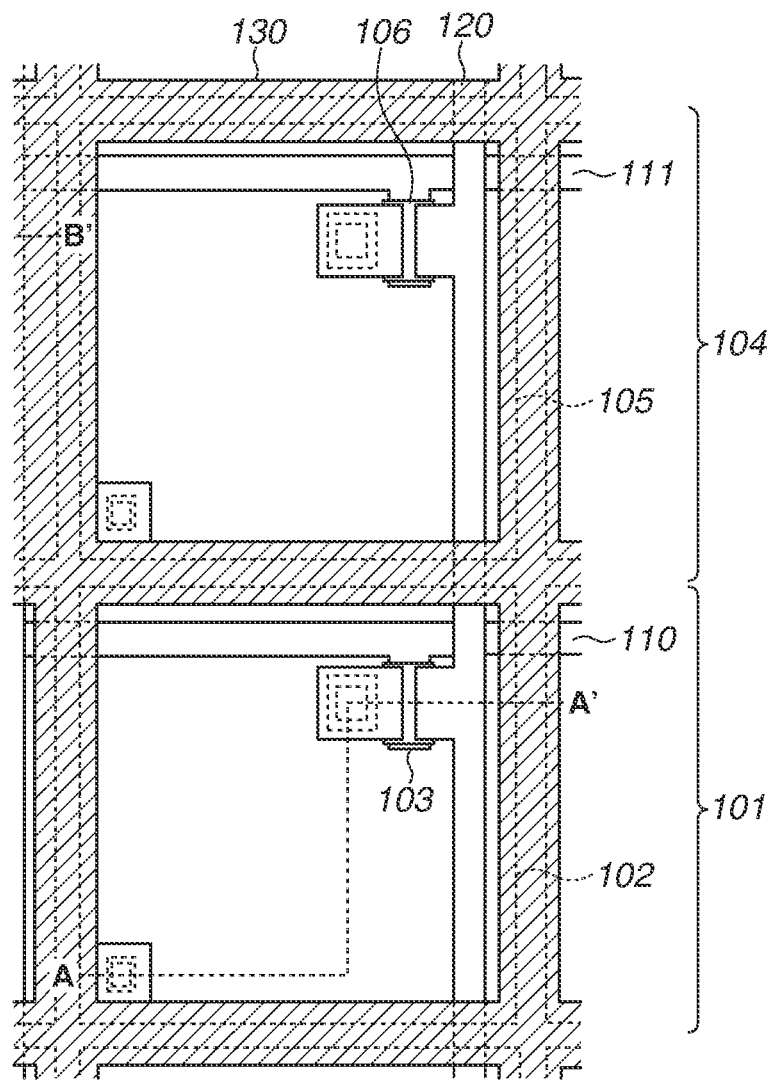
FIG. 3 is a plan view of a configuration of a pixel according to the first exemplary embodiment of the present invention.

An example of the structure of the pixel of the radiation imaging apparatus 100 will be described with reference to FIG. 3 and FIG. 4. FIG. 3 is a plan view of a configuration of each of the imaging pixel 101 and the detection pixel 104 in the radiation imaging apparatus 100. The plan view is equivalent to an orthographic projection on a plane parallel with the imaging region IR of the radiation imaging apparatus 100.

Figure 4:
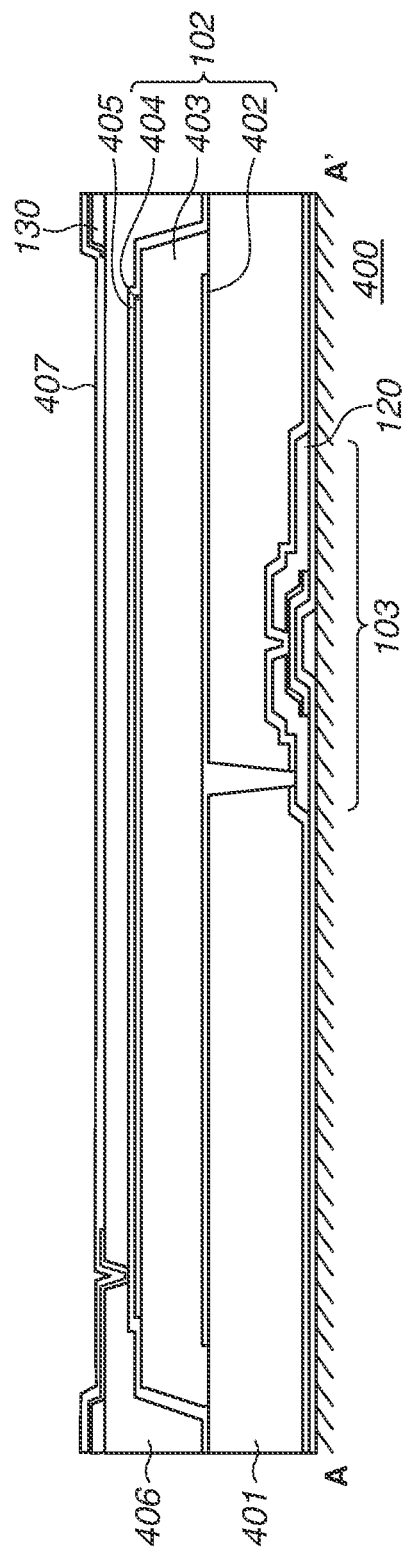
FIG. 4 is a cross-sectional view of a configuration of a pixel according to the first exemplary embodiment of the present invention.

FIG. 4 is a cross-sectional view of the imaging pixel 101 taken along a line A-A' in FIG. 3. A cross sectional view of the detection pixel 104 is similar to the cross-sectional view of the imaging pixel 101. The switch element 103 is disposed on a supporting substrate 400 of insulation, such as a glass substrate. The switch element 103 can be a TFT. An interlayer insulation layer 401 is disposed on the switch element 103. The conversion element 102 is disposed on the interlayer insulation layer 401. The conversion element 102 is a photoelectric conversion element that can convert light into an electrical signal. The conversion element 102 includes, for example, an electrode 402, a PIN photodiode 403, and an electrode 404. Instead of the PIN-type photodiode, the conversion element 102 can be configured of a MIS-type sensor.

A protection film 405, an interlayer insulation layer 406, the bias line 130, and a protection film 407 are disposed in this order on the conversion element 102. A planarization film and a scintillator (neither is illustrated) are disposed on the protection film 407. The electrode 404 is connected to the bias line 130 via a contact hole. As a material of the electrode 404, indium tin oxide (ITO) having light transmission properties is used, and the electrode 404 can transmit light converted from radiation by the scintillator (not illustrated).

Figure 5:
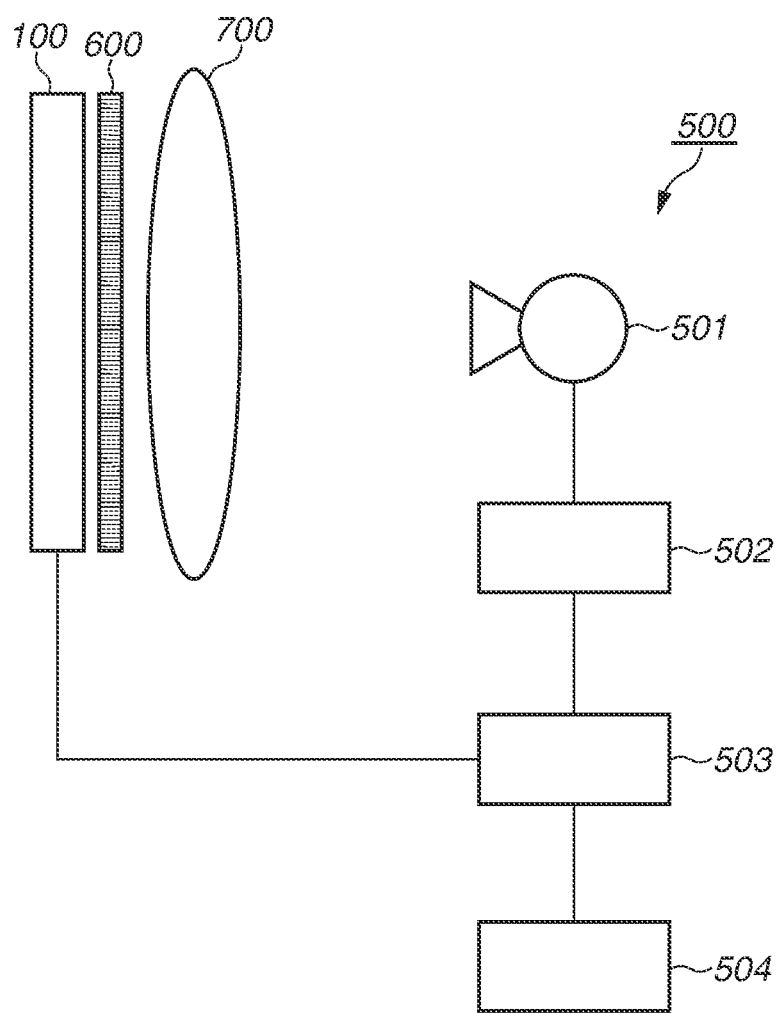
FIG. 5 is a diagram illustrating an example of a configuration of a radiation imaging system including the radiation imaging apparatus according to the first exemplary embodiment of the present invention.

FIG. 5 illustrates an example of a configuration of a radiation imaging system 500 including the radiation imaging apparatus 100. The radiation imaging system 500 includes the radiation imaging apparatus 100, a radiation source 501, a radiation source interface 502, a communication interface 503, a controller 504, a grid 600, and an object 700.

The grid 600 is a sheet having a size close to the size of the radiation imaging apparatus 100 and is disposed between the object 700 and the radiation imaging apparatus 100. The grid 600 is used to remove scattered rays that have passed through the object 700. Desirably, the grid 600 is disposed right in front of the radiation imaging apparatus 100.

A dose, an emission upper limit time (millisecond (ms)), a tube current (milliampere (mA)), a tube voltage (kilovolt (kV)), a region of interest (ROI) that is an area where radiation is to be monitored, and the like are input into the controller 504. When an exposure switch provided on the radiation source 501 is operated, the controller 504 transmits a start request signal to the radiation imaging apparatus 100. The start request signal is a signal that requests a start of emission of radiation. In response to receipt of the start request signal, the radiation imaging apparatus 100 starts preparation to receive radiation to be emitted. When ready, the radiation imaging apparatus 100 transmits a start enable signal to the radiation source interface 502 via the communication interface 503. The start enable signal is a signal notifying that emission of radiation can be started. In response to receipt of the start enable signal, the radiation source interface 502 causes the radiation source 501 to start emission of radiation.

When a threshold for an integrated value of a dose of emitted radiation is reached, the radiation imaging apparatus 100 transmits an end request signal to the radiation source interface 502 via the communication interface 503. The end request signal is a signal requesting an end of the emission of radiation. In response to receipt of the end request signal, the radiation source interface 502 causes the radiation source 501 to end the emission of radiation. The control unit 180 determines the threshold for the dose, based on an input value of dose, a radiation emission intensity, a communication delay between units, a processing delay, and the like. Even in a case where the end request signal is not received, the radiation source 501 stops the emission of radiation when the radiation emission time reaches the input emission upper limit time.

Upon stopping the emission of radiation, the radiation imaging apparatus 100 sequentially scans the driving lines 110 (the driving lines 110 except for the detection driving lines 111) to which the imaging pixels 101 are connected and reads out an image signal of each of the imaging pixels 101 using the reading circuit 160, whereby a radiation image is acquired. Electric charges accumulated in the detection pixel 104 are read out during the emission of radiation, but the signals from these pixels cannot be used to form a radiation image. Thus, the signal processing unit 170 of the radiation imaging apparatus 100 performs interpolation processing using the pixel values of the imaging pixels 101 around the detection pixels 104, whereby the pixel values at the positions of these pixels are interpolated.

Figure 6A:
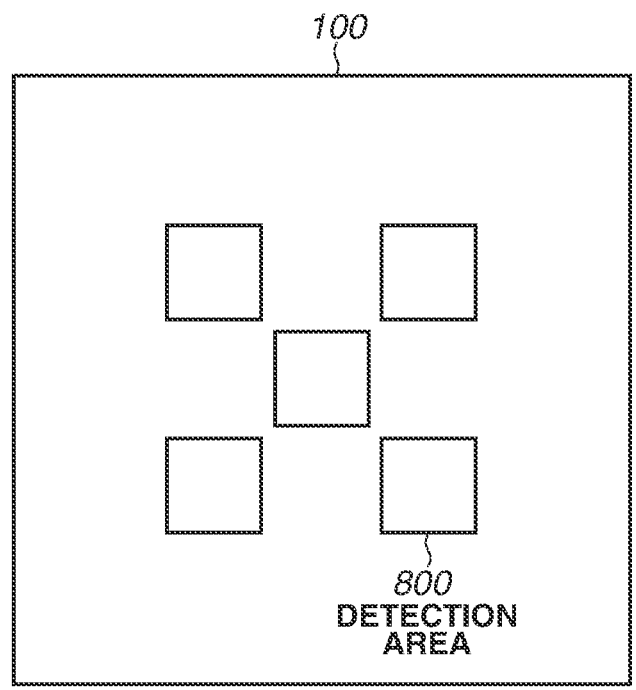
FIGS. 6A and 6B are diagrams illustrating detection areas of the radiation imaging apparatus according to the first exemplary embodiment of the present invention.
Figure 6B:
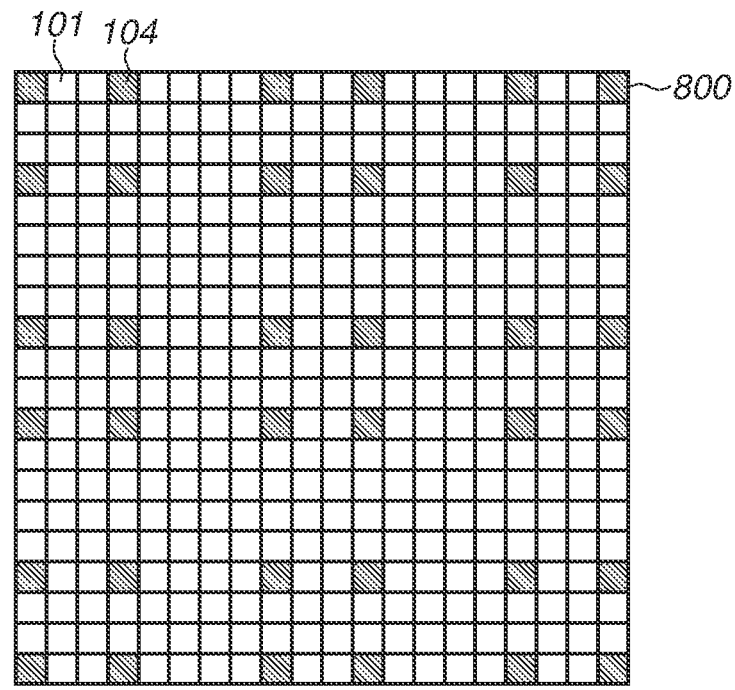

FIGS. 6A and 6B illustrate a detection area 800 in the radiation imaging apparatus 100. The detection area 800 is an area where a dose of radiation during image capturing is detected, and the plurality of radiation detection pixels 104 disposed in the detection area 800 detects the dose of radiation. While there are various methods for arranging a plurality of the detection areas 800, a symmetrical arrangement about the center of the radiation imaging apparatus 100 makes it possible to use the detection areas 800 in the same way irrespective of the orientation of the radiation imaging apparatus 100. The shape of the detection area 800 can be a quadrangle, such as a square and rectangle, or can be a circle or an oval. Further, the detection area 800 can have a shape along the shape of an object. In the AEC, a dose of radiation emitted to a detection area is detected by reading out outputs of a plurality of radiation detection pixels in the detection area during emission of radiation. If an output of imaging pixels in the detection area approximately corresponds to an irradiated dose and the output of imaging pixels in the detection area is approximately equal to an output of the radiation detection pixels read out during the emission, it can be determined that the dose during image capturing is accurately detected, which means that the AEC can be accurately performed. However, depending on a pixel size, an arrangement of the radiation detection pixels, and a grid density (grid pitch), there may be a disproportionate influence of attenuation on the output of the plurality of radiation detection pixels in a region of interest due to an X-ray absorption layer of a grid. In this case, a difference arises between the output of the imaging pixels in the detection area and the output of the radiation detection pixels read out during the emission, which leads to deterioration of the accuracy of the AEC. The plurality of radiation detection pixels 104 in the detection area 800 is arranged in the entire detection area 800, and while there are various arrangement methods, an arrangement method that improves the accuracy of the AEC by reducing or suppressing the disproportionate influence of attenuation due to the X-ray absorption layer of the grid will be described with reference to FIG. 8 to FIG. 11.

FIG. 7 illustrates a configuration of the grid 600. The grid 600 includes a radiation transmissive layer (hereinafter referred to as the X-ray transmissive layer) 601 and a radiation absorption layer (hereinafter referred to as the X-ray absorption layer) 602 each having a strip shape having a length in a first direction, and the X-ray transmissive layer 601 and the X-ray absorption layer 602 are alternately arranged in a second direction. A material easily transmitting X-rays, such as aluminum, is used for the X-ray transmissive layer 601, and a material absorbing X-rays, such as lead, is used for the X-ray absorption layer 602. For example, a grid density D which is the number of the X-ray absorption layers 602 per unit length is 32/centimeter (cm) to 100/cm, and a grid pitch is 100 micrometers ($\mu$m) to about 300 $\mu$m. Depending on a grid density (grid pitch), a pixel pitch, and an arrangement of the radiation detection pixels in the second direction, there may be variations in overlap degrees between the radiation detection pixel and the X-ray absorption layer 602, and consequently the influence of attenuation due to the X-ray absorption layer 602 varies. Further, depending on a degree of the influence on the output of the plurality of radiation detection pixels due to the attenuation by the X-ray absorption layer 602, the accuracy of the AEC changes.

Figure 8:
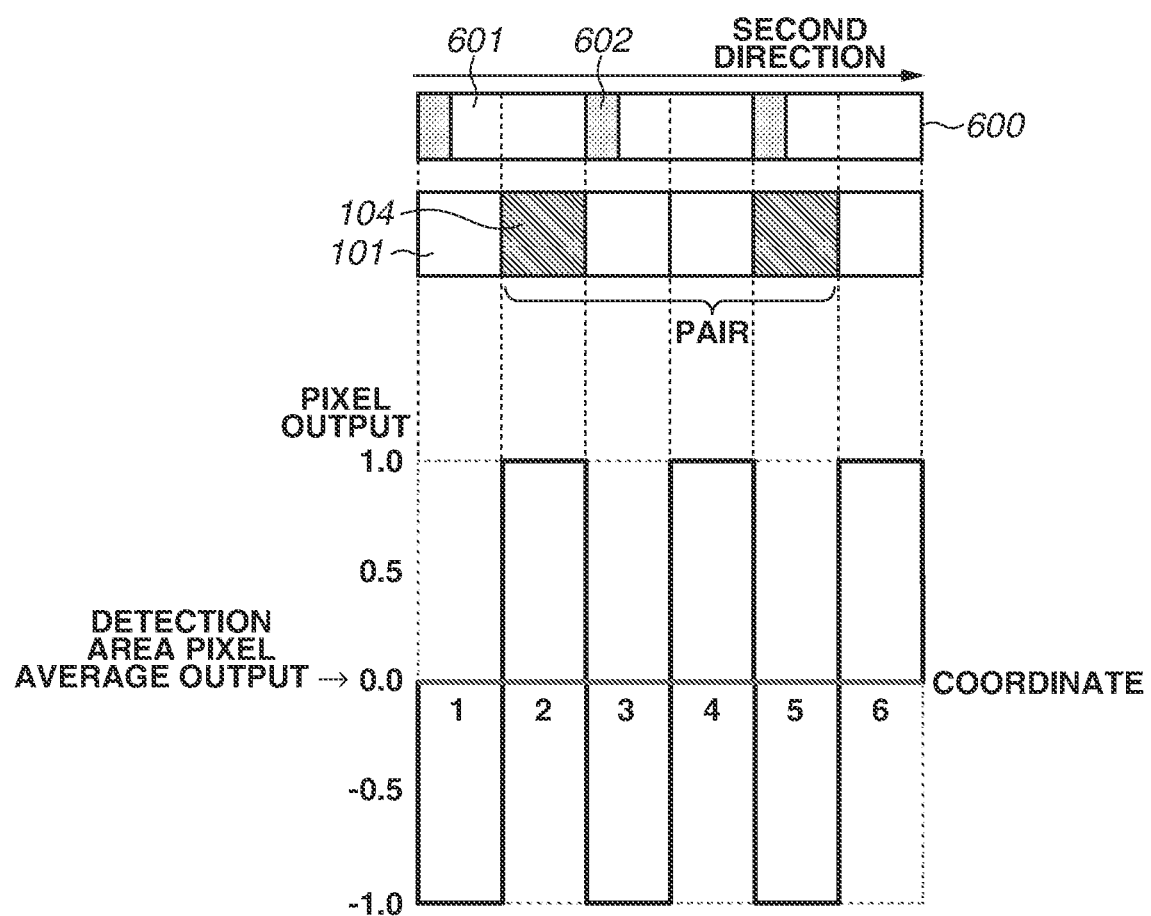
FIG. 8 is a diagram illustrating a pixel arrangement according to the first exemplary embodiment of the present invention.
Figure 9:
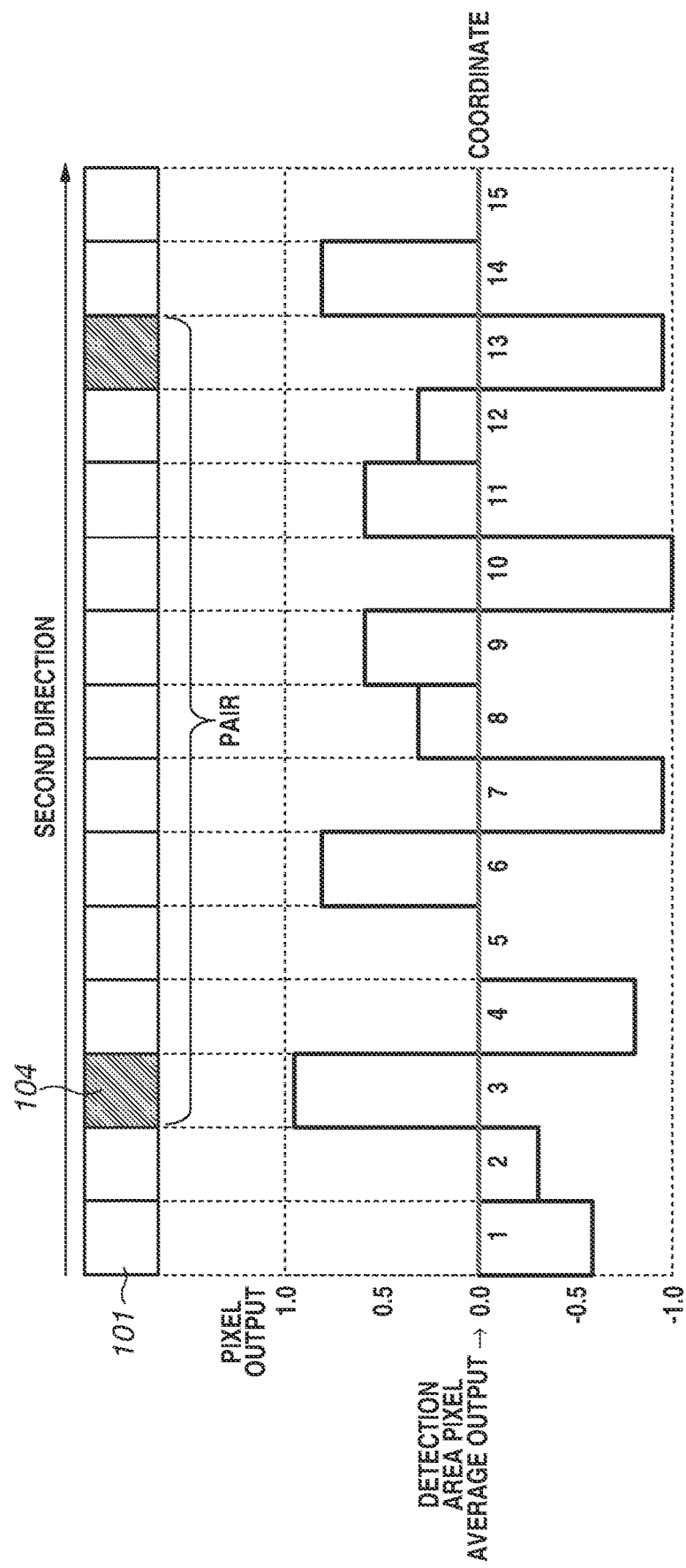
FIG. 9 is a diagram illustrating a pixel arrangement according to the first exemplary embodiment of the present invention.

FIGS. 8 and 9 each illustrate an arrangement of the radiation detection pixels 104 of the grid in the second direction. FIG. 8 illustrates an arrangement and a pixel output of the radiation detection pixels 104 in a case where the pixel pitch is 125 $\mu$m, and the grid density is 40/cm (the grid pitch is 250 $\mu$m). The pixel output indicates a ratio of an output of each of the pixels to an average output of the pixels in the detection area. An output of each of the pixels is affected by a grid disposed in front of the radiation imaging apparatus. The influence of the grid on a pixel output varies depending on a pixel pitch and a grid density (grid pitch). For example, output O which is affected by a grid of the pixels arranged in the second direction of the grid is expressed by the following equation (1):

$$O = \cos(2\pi D/10 \times P \times a) \quad (1),$$

where D represents a grid density (number/cm), P represents a pixel pitch (millimeter (mm)), and a represents a coordinate (integer) representing a position.

While the maximum value of the amplitude of the output O depends on a modulation transfer function (MTF) corresponding to the grid density (number/mm), the maximum value is fixed to 1 in the present invention for simplicity of description. In the case of this combination, the pixel pitch is half of the grid pitch, and thus, as the output of the pixels arranged in the second direction, an output (output −1) obtained with X-ray blocked by the X-ray absorption layer and an output (output 1) obtained with X-ray passed through the X-ray transmissive layer alternately appear in a cycle. For example, in a case where the radiation detection pixel is disposed at each of coordinates 1, 3, 5, and so on, an average output of the plurality of radiation detection pixels is −1 with respect to a detection area pixel average output. In this case, a radiation detection pixel average output is small compared to the detection area pixel average output, and thus the threshold is reached later than the timing at which the threshold is supposed to be reached, which results in excessive emission, and consequently the accuracy of the AEC is deteriorated. In contrast, in a case where the radiation detection pixel is disposed at each of coordinates 2, 4, 6, and so on, the radiation detection pixel average output is 1, which is large compared to the detection area pixel average output. Thus, the threshold is reached before the timing at which the threshold is supposed to be reached, which results in insufficient emission, and consequently the accuracy of the AEC is deteriorated. To address this issue, for example, for the radiation detection pixel having an output (output 1) which is obtained with X-ray passed through the X-ray transmissive layer at the coordinate 2, another radiation detection pixel is disposed at a position having an output (output −1) which is obtained with X-ray blocked in the X-ray absorption layer at the coordinate 5. In this way, two detection pixels are disposed at positions to form a pair. Output signal values of the pair of the two radiation detection pixels are averaged, so that each other's grid influences are canceled, and the detection area pixel average output and the radiation detection pixel average output value become approximately equal, and thus the accuracy of the AEC can be improved by reducing or suppressing the influence of the grid. In other words, the output signal values of the pair of the detection pixels are offset by each other in terms of the influence of the attenuation by the grid and become approximately equal to a detection area pixel average value. Here, being approximately equal to the average value means that differences of about 10% of the average value are included as an allowable range. The outputs of the radiation detection pixels can be used for the total value, instead of the average value.

FIG. 9 illustrates an arrangement and a pixel output of the radiation detection pixels 104 in a case where the pixel pitch is 125 μm, and the grid density is 52/cm (the grid pitch is about 192 μm). In the case of this combination, the pixel pitch and the grid pitch are not integer multiples, and thus, different degrees of influences due to the grid periodically appear as the output of the pixels arranged in the second direction of the grid. Based on the periodicity of the grid influence, for example, for the radiation detection pixel at the coordinate 3, the radiation detection pixel is disposed at the position of the coordinate 13, so that the grid influence can be canceled by an average output of the pair of the two radiation detection pixels. The following equation (2) can express the position of a radiation detection pixel by which the grid influence can be canceled, for a certain radiation detection pixel, based on the periodicity of the grid influence which varies depending on the pixel pitch and the grid density:

$$C=(1+2n)/fg \qquad (2),$$

where $$fg=2|D \times P/10-k|,$$

where D represents a grid density (number/cm), P represents a pixel pitch (mm), k represents an integer satisfying $0 \leq fg \leq 1$, and n represents an integer of 0 or more.

In the case of the pixel pitch of 125 μm and the grid density of 40/cm (the grid pitch of 250 μm) in FIG. 8, k=0 is established, and C=1, 3, 5, and so on is established when n=0, 1, 2, and so on. Thus, the position by which the grid influence can be canceled for the radiation detection pixel at the coordinate 2 is each of the coordinates 3, 5, 7, and so on. In the case of the pixel pitch of 125 μm and the grid density of 52/cm (the grid pitch of about 192 μm) in FIG. 9, k=1 is established, and C=10, 30, 50, and so on is established when n=3, 10, 17, and so on. Thus, the position by which the grid influence can be canceled for the radiation detection pixel at the coordinate 3 is each of the coordinates 13, 33, 53, and so on. In this way, the arrangement of the radiation detection pixels can be determined in accordance with a grid density to be combined with the pixel pitch of the radiation imaging apparatus, based on the equation (2). The radiation detection pixels can be arranged by selecting n so that C becomes an integer, or can be disposed at positions each obtained by rounding off C in a case where C is not an integer. Further, the radiation detection pixel for readout can be selected so that the grid influence can be reduced or suppressed, by changing the detection driving line 111 for driving in image capturing, in accordance with the grid density to be combined with the pixel pitch. In this way, the arrangement of the pair of radiation detection pixels to reduce or suppress the grid influence is determined in accordance with the pixel pitch and the grid density with respect to the periodic grid influence, and thus the grid influence can be canceled even in a case where the output has changed because of a shift of the grid in the second direction. For example, in a case where the grid shifts in the second direction by one pixel in FIG. 9, the output at the coordinates 2 and 12 in FIG. 9 becomes the output of the two radiation detection pixels. In this case as well, the grid influence can be canceled by averaging the output of the two radiation detection pixels. The pair of the two radiation detection pixels can similarly cancel the grid influence, with respect to any shift amount of the grid.

Figure 10:
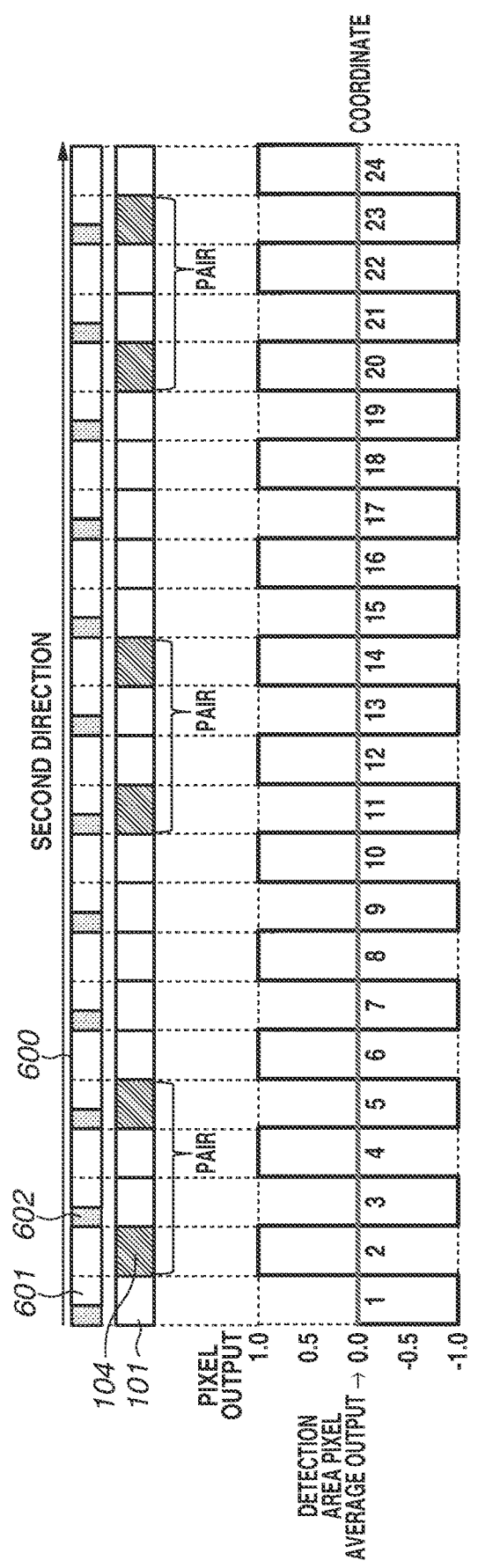
FIG. 10 is a diagram illustrating a pixel arrangement according to a second exemplary embodiment of the present invention.

FIG. 10 illustrates a configuration of a second exemplary embodiment in which a plurality of pairs of radiation detection pixels 104 to reduce or suppress a grid influence is disposed in a detection area. FIG. 10 illustrates an arrangement and a pixel output of radiation detection pixels 104 in a case where a pixel pitch is 125 μm and a grid density is 40/cm (a grid pitch is 250 μm). In FIG. 10, a pair of radiation detection pixels 104 are disposed based on the equation (2), and a plurality of pairs of radiation detection pixels 104 is disposed at regular intervals. In a case where there is a plurality of pairs of radiation detection pixels 104 as well, the influence of the grid is canceled by each pair of radiation detection pixels 104 (coordinates 2 and 5, coordinates 11 and 14, and coordinates 20 and 23), in accordance with the periodicity of the grid influence. Therefore, the grid influence on the output of the plurality of radiation detection pixels 104 in the detection area can be reduced or suppressed, whereby the accuracy of AEC can be improved.

Figure 11:
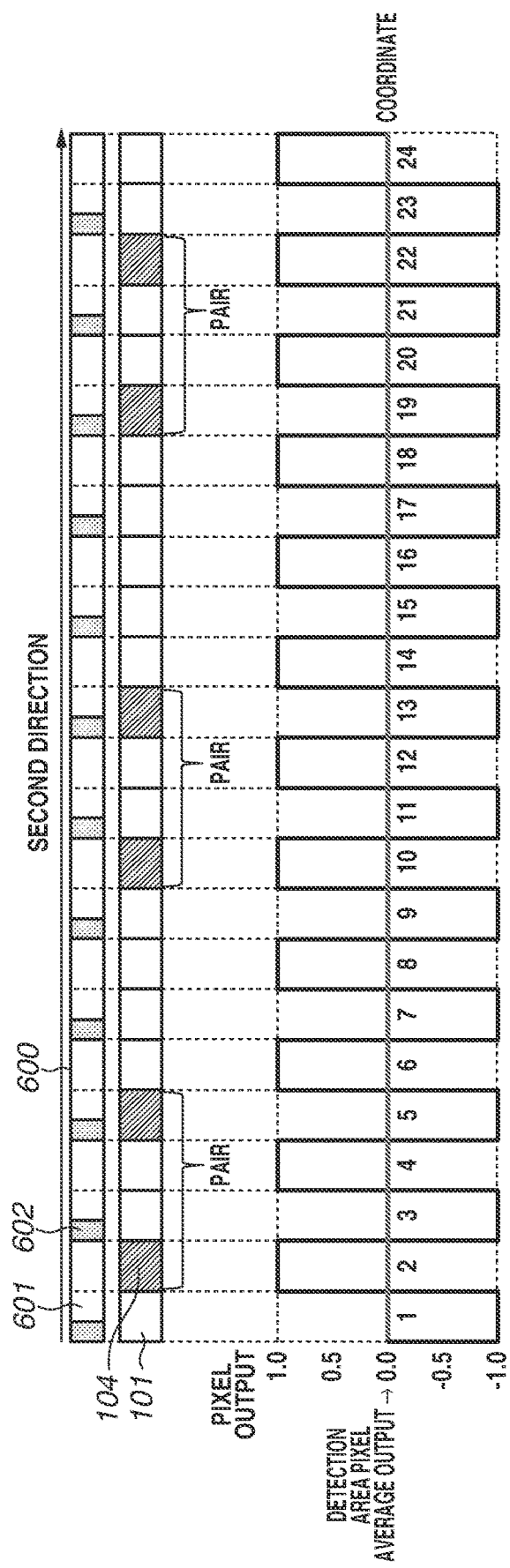
FIG. 11 is a diagram illustrating a pixel arrangement according to a third exemplary embodiment of the present invention.

FIG. 11 illustrates a configuration of a third exemplary embodiment in which a plurality of pairs of radiation detection pixels 104 to reduce or suppress a grid influence is disposed in a detection area. FIG. 11 illustrates an arrangement and a pixel output of radiation detection pixels 104 in a case where a pixel pitch is 125 μm and a grid density is 40/cm (a grid pitch is 250 μm). In FIG. 11, a pair of radiation detection pixels 104 are disposed based on the equation (2), and a plurality of pairs of radiation detection pixels 104 is disposed at different intervals. In a case where pairs of radiation detection pixels 104 are disposed at irregular intervals, the influence of the grid is canceled by each pair of radiation detection pixels 104 (coordinates 2 and 5, coordinates 10 and 13, and coordinates 19 and 22), in accordance with the periodicity of the grid influence. Therefore, the grid influence on the output of the plurality of radiation detection pixels 104 in the detection area can be reduced or suppressed, whereby the accuracy of AEC can be improved. The case where the pairs of radiation detection pixels 104 are disposed at irregular intervals means a case where pairs of detection pixels are aperiodically arranged.

Figure 12:
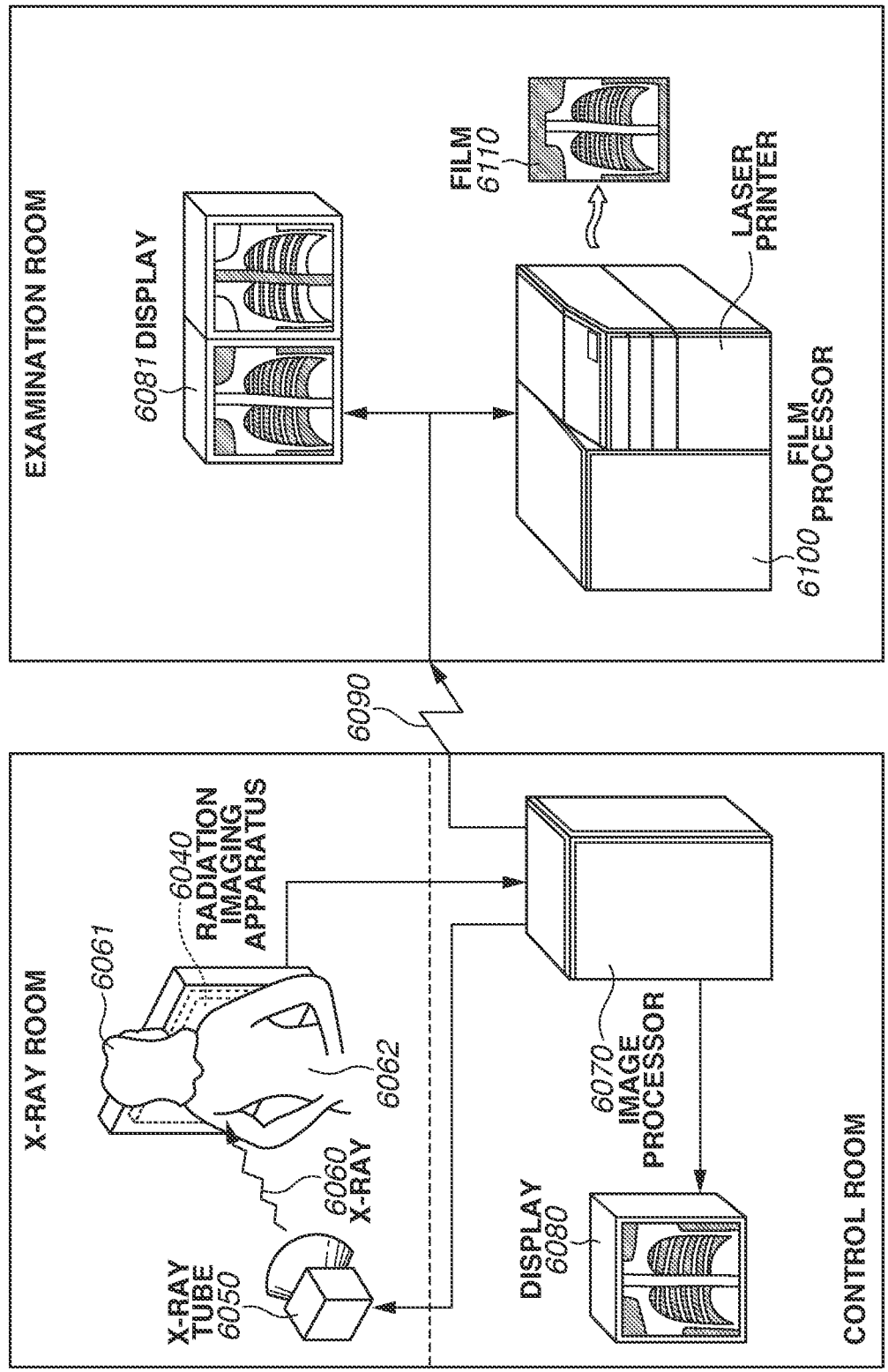
FIG. 12 is a diagram illustrating an example of a configuration of a radiation imaging system.

An example in which the radiation imaging apparatus 100 is applied to a radiation detection system will be described below with reference to FIG. 12. An X-ray 6060 generated by an X-ray tube 6050 that is a radiation source passes through a chest 6062 of a patient or subject 6061 and is incident on a radiation imaging apparatus 6040 represented by the radiation imaging apparatus 100 described above. The incident X-ray includes information about the inside of the body of the subject 6061. The scintillator emits light in response to the incidence of the X-ray, and the photoelectric conversion element photoelectrically converts the light, whereby electrical information is obtained. The information is converted into digital information, and the digital information is subjected to image processing by an image processor 6070 that is a signal processing unit. The processed information is displayed on a display 6080 of a display unit in a control room, whereby the user can observe the image.

In addition, the information can be transferred to a remote location by a transmission processing unit using, for example a telephone line 6090, and the transferred information can be displayed on a display 6081 of a display unit or saved into a recording unit, such as an optical disc, in an examination room at another place, which can allow a doctor to make diagnosis at the remote location. The information can also be recorded in a film 6110 that is a recording medium recorded by a film processor 6100 serving as a recording unit.

According to the exemplary embodiments of the present invention, it is possible to improve the accuracy of automatic exposure control, by reducing or suppressing a disproportionate influence on a signal of a radiation detection pixel due to attenuation by an X-ray absorption layer of a grid.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-192186, filed Nov. 26, 2021, which is hereby incorporated by reference herein in its entirety.

What is claimed is:

1. An x-ray radiation imaging apparatus that is able to perform radiography using a grid in which an x-ray radiation transmissive layer and an x-ray radiation absorption layer each having a strip shape and extending in a first direction are alternately arranged in a second direction, the x-ray radiation imaging apparatus comprising:
a pixel unit including a plurality of imaging pixels for acquiring an x-ray radiation image and a plurality of detection pixels for detecting a dose of x-ray radiation that are disposed in an imaging region;
a driving unit configured to drive the plurality of imaging pixels and the plurality of detection pixels;
a reading unit configured to read out a signal from each of the plurality of imaging pixels and the plurality of detection pixels; and
a control unit configured to determine an amount of x-ray radiation being emitted to the x-ray radiation imaging apparatus,
wherein the plurality of detection pixels includes a first detection pixel and a second detection pixel that are in a pair in the second direction, an output signal value of the first detection pixel is larger than an average value of output signal values of the plurality of imaging pixels and the plurality of detection pixels, and an output signal value of the second detection pixel is smaller than the average value,
wherein a plurality of pairs of the first detection pixel and the second detection pixel is disposed in an aperiodic arrangement.

2. The x-ray radiation imaging apparatus according to claim 1, wherein the average value of the output signal values of the plurality of imaging pixels and the plurality of detection pixels is an average value of output signal values of imaging pixels and detection pixels disposed in a detection area that is an area where x-ray radiation is detected.

3. The x-ray radiation imaging apparatus according to claim 1, wherein an average value of the output signal values of the first detection pixel and the second detection pixel is equal to the average value of the output signal values of the plurality of imaging pixels and the plurality of detection pixels.

4. The x-ray radiation imaging apparatus according to claim 1, wherein the first detection pixel and the second detection pixel are disposed, in the second direction, at respective positions satisfying the following equation:

$$C = (1+2n)/fg,$$

where $$fg = 2|D \times P/10 - k|,$$

where C represents a position of the second detection pixel with respect to the first detection pixel, D represents a grid density (number/centimeter), P represents a pixel pitch (millimeter), k represents an integer satisfying $0 \leq fg \leq 1$, and n represents an integer of 0 or more.

5. An x-ray radiation imaging apparatus comprising:
a pixel unit including a plurality of imaging pixels for acquiring an x-ray radiation image and a plurality of detection pixels for detecting a dose of x-ray radiation that are disposed in an imaging region;
a driving unit configured to drive the plurality of imaging pixels and the plurality of detection pixels;
a reading unit configured to read out a signal from each of the plurality of imaging pixels and the plurality of detection pixels; and
a control unit configured to determine an amount of x-ray radiation being emitted to the x-ray radiation imaging apparatus,
wherein the plurality of detection pixels includes a first detection pixel and a second detection pixel, and when radiography is performed using a grid in which an x-ray radiation transmissive layer and an x-ray radiation absorption layer each having a strip shape and extending in a first direction are alternately arranged in a second direction, the first detection pixel and the second detection pixel are disposed in a pair in the second direction in such a manner that an output signal value of the first detection pixel is larger than an average value of output signal values of the plurality of imaging pixels and the plurality of detection pixels and an output signal value of the second detection pixel is smaller than the average value,
wherein a plurality of pairs of the first detection pixel and the second detection pixel is disposed in an aperiodic arrangement.

* * * * *